United States Patent
Kaufmann

(10) Patent No.: US 8,002,820 B2
(45) Date of Patent: Aug. 23, 2011

(54) MARKER ELEMENT FOR THE PRECISE IMPLANTATION OF STENTS

(75) Inventor: Ralf Kaufmann, Rangendingen (DE)

(73) Assignee: Jotec GmbH, Hechingen (DE)

( * ) Notice: Subject to any disclaimer, the term of this patent is extended or adjusted under 35 U.S.C. 154(b) by 680 days.

(21) Appl. No.: 11/880,186

(22) Filed: Jul. 19, 2007

(65) Prior Publication Data

US 2008/0051870 A1 Feb. 28, 2008

(30) Foreign Application Priority Data

Jul. 19, 2006 (DE) .......................... 10 2006 033 399

(51) Int. Cl.
*A61F 2/06* (2006.01)
(52) U.S. Cl. ...................................... 623/1.34; 623/1.11
(58) Field of Classification Search ................. 623/1.15, 623/1.34, 1.2, 1.11, 1.12; 606/108
See application file for complete search history.

(56) References Cited

U.S. PATENT DOCUMENTS

| 4,733,665 | A | * | 3/1988 | Palmaz ........................ 606/108 |
| 5,725,572 | A | | 3/1998 | Lam et al. |
| 6,027,509 | A | * | 2/2000 | Schatz et al. .................. 606/108 |
| 6,264,671 | B1 | * | 7/2001 | Stack et al. ................... 606/198 |
| 6,409,752 | B1 | | 6/2002 | Boatman et al. |
| 6,447,540 | B1 | * | 9/2002 | Fontaine et al. ............ 623/1.12 |
| 6,676,667 | B2 | * | 1/2004 | Mareiro et al. ............... 606/108 |
| 6,699,274 | B2 | * | 3/2004 | Stinson ........................ 623/1.12 |
| 7,264,632 | B2 | * | 9/2007 | Wright et al. ................. 623/1.12 |
| 7,309,351 | B2 | * | 12/2007 | Escamilla et al. ........... 623/1.12 |
| 7,473,271 | B2 | * | 1/2009 | Gunderson .................. 623/1.12 |
| 2002/0082683 | A1 | * | 6/2002 | Stinson et al. ............... 623/1.23 |
| 2002/0091439 | A1 | | 7/2002 | Baker et al. |
| 2004/0204749 | A1 | * | 10/2004 | Gunderson .................. 623/1.12 |
| 2006/0100688 | A1 | | 5/2006 | Jordan et al. |

FOREIGN PATENT DOCUMENTS

| DE | 101 55 191 | 5/2003 |
| DE | 103 35 649 | 2/2005 |
| EP | 0 858 299 | 3/2002 |
| EP | 0 684 022 | 2/2004 |
| EP | 1 466 570 | 10/2004 |
| WO | WO-98/57692 | 12/1998 |
| WO | WO-99/49812 | 10/1999 |
| WO | WO-00/71058 | 11/2000 |
| WO | WO-01/35862 | 5/2001 |

* cited by examiner

*Primary Examiner* — David Isabella
*Assistant Examiner* — Jason-Dennis Stewart
(74) *Attorney, Agent, or Firm* — Morrison & Foerster LLP

(57) ABSTRACT

The present invention concerns a marker element (1) for marking one or more boundaries of a section of a stent (2) with a mesh (20), the marker element (1) including a radiopaque material and being fitted on a device (5) for the delivery of the self-expanding stent (2) into a body vessel, the device (5) including a tubular element (6) which is inserted through the stent (2). The marker element (1) between the stent (2) and the tubular element (6) can slide on the tubular element (6) and engages detachably into the mesh (20) of the stent (2). The invention further concerns a device (5) for the delivery of a self-expanding stent (2) into a body vessel which is fitted with a marker element (1) of this type.

10 Claims, 4 Drawing Sheets

MARKER ELEMENT FOR THE PRECISE IMPLANTATION OF STENTS

This application claims priority under 35 U.S.C. §119(d) from German Patent Application No. 10 2006 033 399.3, filed Jul. 19, 2006. The content of the above patent application is incorporated by reference herein in its entirety.

The present invention concerns a marker element for marking one or more boundaries of a section of a self-expending stent with a mesh, the marker element including radiopaque material and being fitted on a device for introducing the stent into a body vessel, the device including a tubular element which is inserted through the stent.

Markers or marker elements containing radiopaque material are used when the delivering stents into a patient's body vessels to permit monitoring of the position of the stent and/or the delivery device by fluoroscopy and precise monitoring of the introduction and release.

Stents are endoprostheses made of various materials which are generally used to maintain the patency of body vessels, and comprise tubular and/or mesh structures with or without coatings. Stents are introduced into the vessels in a compressed form using a suitable delivery system and unfold in the target position, where they are to remain. The walls of the stent press intraluminally against the walls of the vessel. Self-expanding stents can, for example, be compressed for introduction into a vessel by an outer sleeve which is withdrawn after correct positioning so that the self-expanding stent can unfold and expand as a result of its elasticity.

The fitting of radiopaque markers on a system for the introduction of stents into a body vessel in the form of ring-shaped or tubular structures on the appropriate functional elements—the outer sleeve, guide wire catheter or pusher—which are glued firmly in place or held in place by precision forming, so-called "swaging", is known from the prior art. Markers for delivery systems in which radiopaque substances are introduced into the extrusion or moulding compound before manufacture of the functional elements are also known.

All these markers are used to monitor the position in the body and to check the function of the devices during implantation of the stent.

When necessary, radiopaque markers are also affixed to the stents themselves. Markers which are pressed, welded, soldered or glued into appropriate eyelets in laser-cut stents are known from the prior art. U.S. Pat. No. 6,409,752 describes such a method of attachment.

The markers are generally used to mark the ends of stents under fluoroscopy. Thus, it is generally possible to mark special stent zones with specific mechanical-physical, chemical or biological properties in the central region of the stent as well, because virtually no structures or boundaries can be identified on a stent in the folded state.

U.S. Pat. No. 5,725,572 describes another way of marking the ends of stents with a radiopaque material applied locally to the stent as a thin layer. This can be done by targeted vapour deposition or by the precipitation of radiopaque substances at defined points on the stent. The radiopaque markers should in all cases, as intended, be impossible to detach from the stent.

In addition, WO 98/57692 discloses an expandable stent and a system for introducing this stent into a body cavity which has an inner and an outer tube. The delivery system described in this international patent application has, among other things, ring-shaped radiopaque markers firmly attached to the outer and inner tubes which are used to hold the outer sleeve which compresses the stent. The two markers firmly attached to the inner tube mark the two ends of the stent. By moving the tubes with respect to each other, the outer sleeve is removed from the stent, and the latter is released.

In contrast to laser-cut stents, the prior art for self-expanding stents made of individual woven wires, so-called woven stents, describes no or only inadequate methods of local quasi-zero-dimensional X-ray marking for the visualization of the ends of stents or the boundaries of special zones of the stent with specific mechanical-physical, chemical or biological properties under fluoroscopy.

A wire-woven stent of this type with a special—so-called functional—zone, in this case characterized by its particular mechanical-physical properties, is described in patent application DE 103 35 649, to which reference is herewith expressly made. The term "functional zone", here and below, is taken to mean a region of the stent, preferably in the central section of the stent, which has a lower weaving angle than in the adjoining sections along the longitudinal axis, preferably the proximal and distal sections.

With stents of this type, the problem arises that they become much shorter when they are released. The ratio l/L of the stent length l in the loaded state to the free stent length L depends on the internal diameter d of the outer sleeve, the diameter D of the stent in the deployed state and the weaving angle $\alpha$. For example, a stent of length L=40 mm, diameter D=6 mm and a weaving angle $\alpha$=40°, when it is compressed to d=1.5 mm, is a factor of 1.53 longer. For a stent with a functional zone with a weaving angle of e.g. $\alpha$=10°, the increase in length in the outer sleeve of the delivery system can even be a factor (l/L) of 4 to 6.

A usable, sharply defined or quasi-zero-dimensional (i.e. quasi point-shaped) marking on a woven stent for the precise labelling of certain functional zones, required for exact positioning in a vascular lesion, has not hitherto been described. In the prior art, only the attachment of radiopaque materials to the ends of the wires by welding, soldering or gluing, as shown e.g. in the technique described in EP 0 858 299, is known.

In addition, hollow cylindrical X-ray markers can be threaded through the weave wires in the middle of the stent before weaving and then crimped or glued in place, but this method has considerable disadvantages.

For example, local quasi-zero-dimensional markers must have a very high X-ray density and an adequate volume to be clearly visible with normal fluoroscopes currently available. Stents, for example those intended for uses including cerebral or intracranial blood vessels, which are sometimes very thickly woven from very thin wires 0.05 mm to 0.1 mm in diameter, do not offer enough possible anchor points for a voluminous X-ray marker of adequate visibility.

Quasi-zero-dimensional markers can also often only be attached after production and surface treatment of the stent, as their chemical and mechanical properties have a negative effect on the treatment of the stent, for example, as a result of thermomechanical processes and surface polishing techniques.

The electrochemical interactions between the stent material and a locally concentrated marker material in blood or other body fluids can lead to detachment of the connection and to corrosion of the stent itself. The resultant risk of embolic cerebral stroke caused by fragments of stent or marker material released thereby is not acceptable.

Quasi-zero-dimensional markers must also withstand the large changes in shape of the woven structure of the stent when it is deployed, particularly the shortening to as little as one sixth of its length described above, and must not damage the inner wall of the filigreed delivery system, which can have an internal diameter of 0.9 mm to 1.8 mm. Particles of the delivery system formed by such abrasion could also cause embolic cerebral strokes in patients.

Finally, assembly and bonding techniques such as gluing, soldering, welding and crimping of quasi-zero-dimensional markers in the middle region of woven stents would require new and possibly complex production procedures.

The object on which the invention is based, therefore, is to render one or both boundaries of a section of a self-expanding stent with a mesh in the delivery system clearly and distinctly visible by fluoroscopy during its deployment in a simple and safe manner.

This object is achieved according to the invention by ensuring that the marker element between the stent and the tubular element is fitted on such that the marker element can slide on the tubular element and engages detachably into the mesh of the stent.

The object on which the invention is based is completely solved in this way.

With the marker element according to the invention, it is possible to also mark sections of a stent which change length during deployment of the stent, during its positioning and deployment. This is achieved by the marker element being connected in a form-fit, but detachable, manner to the stent loaded in the delivery system, or engaging detachably into the mesh of the stent, when the latter is in the compressed state, i.e. loaded in the delivery system.

At the same time, the marker element can slide backwards and forwards on the guide wire catheter, namely between the guide wire catheter and the stent, but cannot become detached from the guide wire catheter. The marker element can thus be attached to the stent at one point, where it is intended to mark e.g. the start or end of a stent zone with special mechanical-physical, chemical or biological properties under fluoroscopy, in a detachable manner.

The term "self-expanding stent" is taken to mean any stent or stent graft the framework of which, e.g. a wire framework, is made of a self-expanding material, in which the framework can also be connected to a textile tube. For implantation into a vessel in the body, the stent can be radially compressed, e.g. by an outer sleeve, so that its cross-sectional area is substantially reduced and it can be easily introduced into the vessel; when the compression is released, that is, when e.g. the outer sleeve is removed, the stent unfolds radially to its original shape because of the spring action of its framework, and becomes lodged inside the body vessel.

"One or more boundaries of a section of a self-expanding stent" can—on the one hand—mean one or the other end of the stent, i.e. the section in this case is defined as the entire stent. Alternatively, however, it can mean a particular section within the stent which is distinguished from the other sections of the stent in respect of its different mechanical-physical, chemical or biological properties. This may e.g. be a so-called functional zone of a woven stent, as disclosed and defined in DE 103 35 649 for example. DE 103 35 649 discloses a woven stent with a woven structure made up of a large number of thread-like elements which, in the expanded state of the woven stent, intercept a plane at right angles to the longitudinal direction at a certain weaving angle. The stent has a zone (hereinafter referred to as the "functional zone") which has a smaller weaving angle than in the neighbouring sections or zones of the woven stent. In this connection, therefore, "a boundary of a section" would mean the end(s) of the functional zone.

"Radiopaque material" means the presence of any material which is opaque or only slightly transparent to X-rays and which is therefore visible when using appropriate imaging procedures, e.g. X-ray fluoroscopy, e.g. as a spot. With the marker element according to the invention the disadvantages of the prior art can be avoided and a fluoroscopically clear and distinctly visible marking is provided at one or both ends of a section of a self-expanding stent with a mesh during its positioning and deployment in a body vessel.

The marker element may be formed from a single piece or several components joined together.

The marker element, which contains an adequate mass of radiopaque material, is positively anchored to the stent inside the loaded stent at the point of the boundary to be marked.

In one embodiment it is preferable for the tubular element to be a guide wire catheter. In this case, the stent for introduction into a body vessel is loaded in a device for delivering the stent which includes, among other things, a guide wire catheter, and the marker element is mounted such that it can slide between the guide wire catheter and the stent on the guide wire catheter, with the marker element engaging into the mesh of the stent.

When, therefore, the stent moves during its deployment within the delivery device, the marker element moves position with it. Only when the marked section of the stent leaves the outer sleeve and that part of the stent detaches from the delivery system because of its self-expanding properties, does it simultaneously detach from the marker element which is arranged on the guide wire catheter and is connected to the latter such that it can slide on it but cannot become detached from it.

The marker is thus available for use during positioning and implantation of the stent as if it were part of the stent itself, but after deployment of the stent it becomes part of the delivery device and is removed from the body with the latter. This construction permits quasi-zero-dimensional markers with a very high X-ray density and an adequate volume to be realized on the stent.

Stents made of extremely thin wires 0.05 mm to 0.1 mm in diameter and are very densely woven will no longer require, anyway inadequate, anchor points for relatively voluminous X-ray markers.

During the manufacture and treatment of the stents, there is no need to take into account complex chemical and mechanical interactions with the radiopaque material resulting from theromechanical processes and surface polishing procedures.

The electrochemical interaction between the stent material and locally concentrated marker material, and the associated risk of embolic cerebral stroke brought about by particles of stent and marker released by corrosion is avoided.

The quasi-zero-dimensional markers can withstand the large changes in shape of the woven structure of the stent during its deployment, particularly the shortening in an extreme case down to one sixth of its length in the loaded state and, as a result of its position inside the folded stent, cannot damage the inner wall of the filigreed device or delivery system.

The advantage of this is that the marker element with its close fit with the compressed stent marks the start or end of a functional zone of the stent even if the functional zone moves axially with respect to the guide wire catheter during deployment of the stent.

For follow-up examinations, in which individual images are generally obtained using stationary and more powerful X-ray machines, the substantially more dense weave of the functional zones described here are sufficiently differentiated.

In another embodiment, it is preferable for the marker element to have a hollow anchor element which in turn has at least one, preferably 1 to 12, radially outward-pointing projection which engages into the mesh of the stent.

This embodiment has the advantage that the projection or projections form a sort of anchor element or elements that engage into the stent and anchor to it.

For this purpose, prismatic or pyramidal projections could be formed. In the case of the formation of projections/anchors as prismatic bodies, it is preferable if these are formed with the front face towards the hollow cylindrical body. In the case of the formation of projections/anchors as truncated pyramids, it is preferable if the larger face of these is directed towards the hollow cylindrical body.

It is particularly preferable for the heights of the projections/anchors to be of such a size that the marker element has sufficient play with respect to the outer sleeve, but heights which are less than the wall or weave-wire thickness of the stent, so that the stent in the compressed state cannot slip off the marker element.

The invention also concerns a device for the delivery of a self-expanding stent in a body vessel, the device having the following components:
- an outer sleeve which holds a stent under radial compression in a distal section of the delivery system,
- a pusher guided through the outer sleeve with its distal end pushing against the proximal end of the stent,
- a tubular element, preferably a guide wire catheter, which passes through the compressed stent and the pusher, which also has a marker element which is arranged on the tubular element such that it can freely slide backwards and forwards but cannot become detached and is connected to the radially compressed stent in a detachable manner.

In particular, it is preferable if the device has a marker element as described above.

In another embodiment, it is preferable if the device according to the invention has an outer sleeve which has an outer sleeve marker. It is obvious that the marker element can be attached in a slideable manner to any tubular or conical element on to which a stent for introduction into a body vessel is to be loaded. What is important for the present invention is that the marker element can engage into the stent in a detachable manner, and that it can slide on, but is fitted to the tubular element in a non-detachable manner, and is thus located between the stent and the tubular element.

As the radiopaque material, it is possible to use any radiopaque material known from the prior art which proves to be suitable for the present purpose. Suitable materials are e.g. heavy biocompatible metals, e.g. the noble metals gold, platinum, iridium or platinum-iridium, but also metals such as tantalum; though it will be clear to a person skilled in the art that other materials not listed here could be used for the marker element according to the invention.

The device according to the invention, i.e. the delivery system, has an outer sleeve which holds the stent in radial compression. When the outer sleeve is drawn back proximally, it releases the stent from the distal end to the proximal end, so that, as a result of its self-expanding mechanism, the stent becomes detached from the device and the sliding marker elements attached to it. After deployment of the stent, the delivery system together with the sliding marker elements attached to it is withdrawn from the body vessel.

The term "distal" in this case designates the direction/end of the device or parts of the device leading away from the operator (that is, in the direction of the tip of the delivery system); the term "proximal" designates the direction/end of the device or parts of the device leading or pointing towards the operator.

An example of an embodiment of the invention is shown in the drawings and will be discussed in more detail in the description below. In the drawings.

Figure 1:
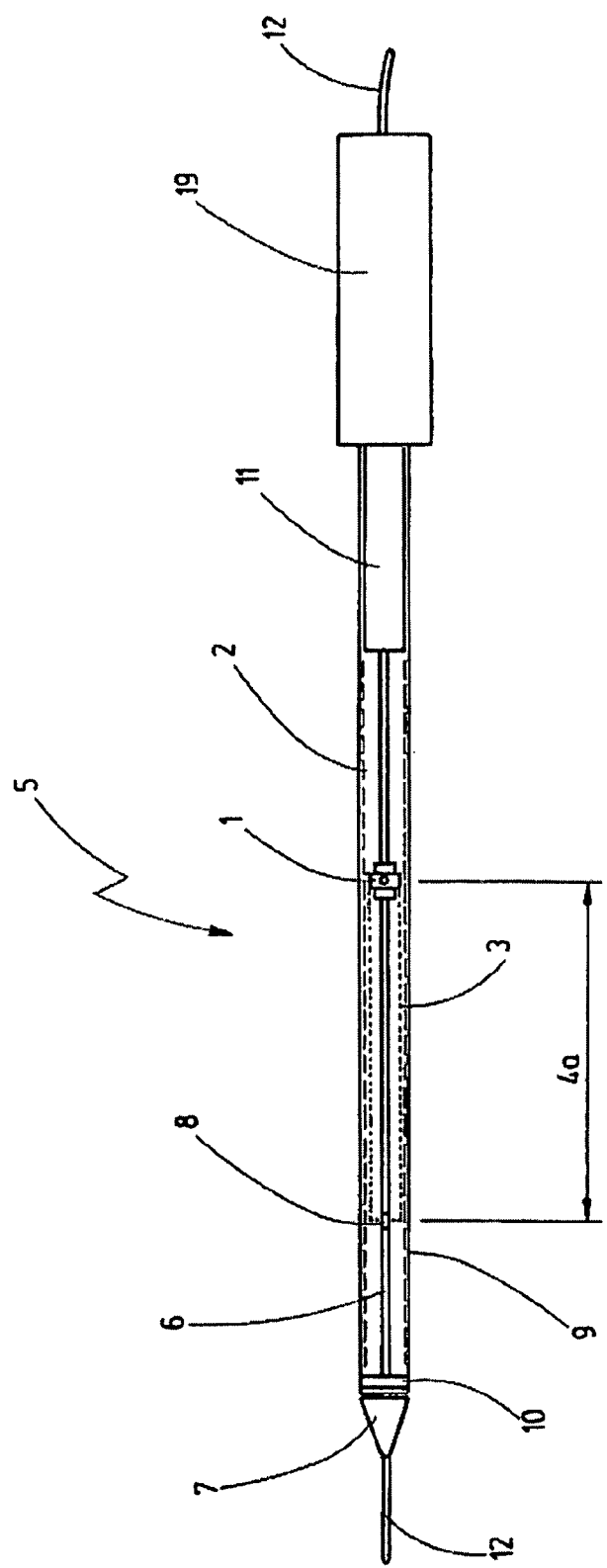
FIG. 1 shows a schematic representation of an embodiment of a delivery system according to the invention with loaded stent, which is not intended to be true to scale, in which the outer sleeve is transparent and the stent is only shown as a dashed line and its functional zone only by a dotted line.

In FIG. 1, reference number 5 designates the entire—schematic—delivery system or device for the delivery of the stent, with 2 indicating the stent—which has a functional zone indicated by 3—which can be introduced into a body vessel or blood vessel.

The stent 2 can be a self-expanding metal stent, produced using the weaving technique, as described in DE 103 35 649, mentioned in the introduction. The delivery system 5 has a handle 19, which is functionally connected to an outer sleeve 9, a pusher 11, and a guide wire catheter 6. The outer sleeve 9 holds the stent 2 in radial compression. The outer sleeve 9 has an outer sleeve marker 10 of radiopaque material at its distal end.

In this state, the delivery system 5 is introduced into a vessel along a guide wire 12 by the known Seldinger method. The guide wire 12 passes through the atraumatic tip 7 and the guide wire catheter 6 inside the stent 2 and the delivery system 5. The guide wire catheter 6 also passes through the pusher 11 (not shown here).

A guide wire catheter marker 8 is attached to the guide wire catheter 6 by the methods described at the start. The movable marker element 1 according to the invention is also located on the guide wire catheter 6, which is very useful for the stent concerned.

The movable marker element 1 and the fixed guide wire catheter marker 8 delimit the functional zone 3 of the stent 2 in the delivery system 5. In another embodiment, which is not shown here, the distal boundary marker can also be designed to slide on the guide wire catheter in the same way as the marker element 1.

4a indicates the length of the functional zone 3 of the stent 2 in the delivery system 5. When the delivery system 5 or the folded stent 2, or rather the functional zone 3 is positioned in the target vascular lesion, the stent 2 is released distally by drawing the outer sleeve 6 back proximally and simultaneously pushing the pusher 11 distally.

Figure 2:
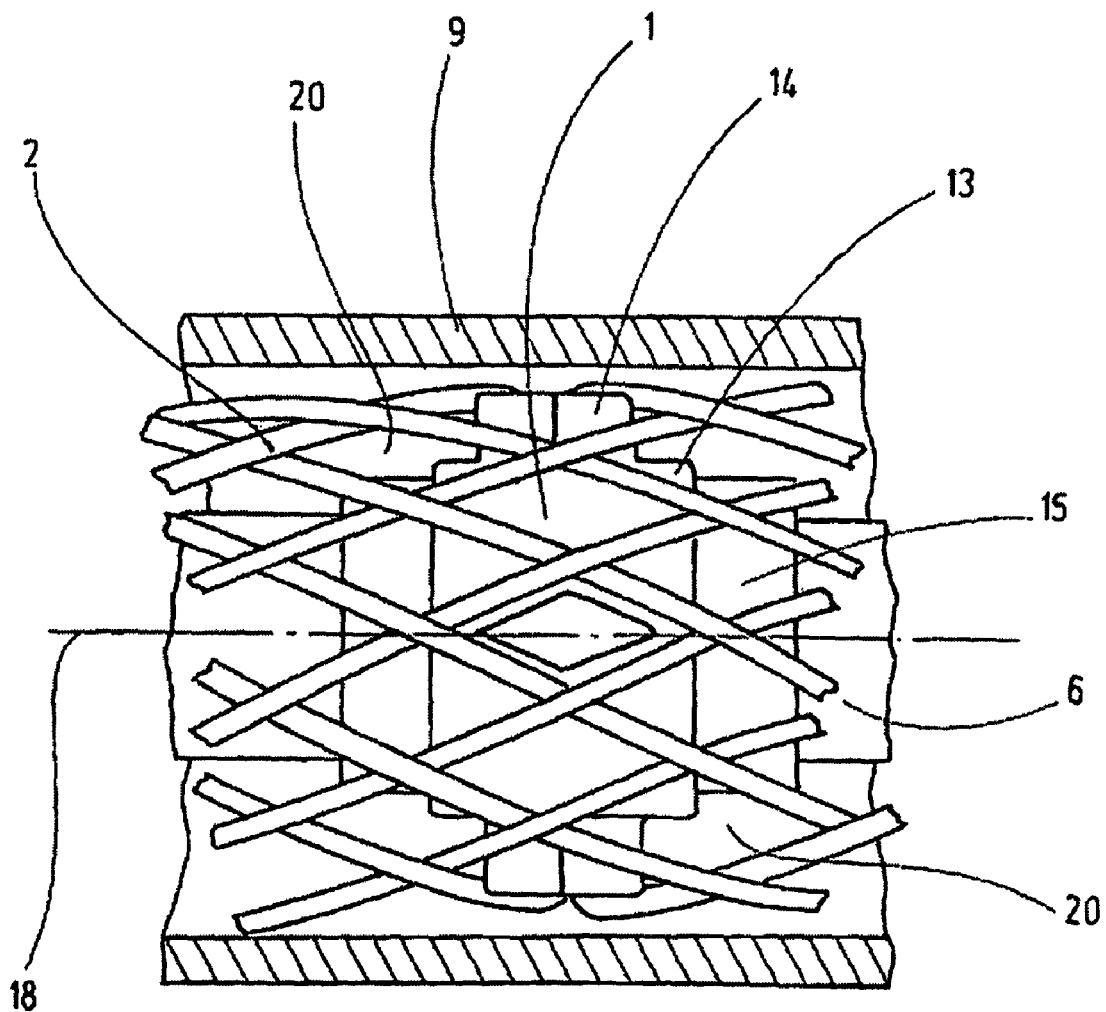
FIG. 2 shows a section of an enlarged, schematic, view, which is not true to scale, of an embodiment of the marker element according to the invention in the delivery system from FIG. 1, with only the outer sleeve in longitudinal section.

FIG. 2 is an enlarged, schematic, view, which is not true to scale, of an exemplary embodiment of the marker element 1 in the delivery system 5 from FIG. 1, with only the outer sleeve 9 in longitudinal section. The marker element 1 is located inside the compressed stent 2, which has a mesh 20, and is threaded round the guide wire catheter 6 like a ring.

The marker element 1 comprises a hollow cylindrical body 13 which can have one to twelve radially outward-pointing projections/anchors 14, depending on the embodiment. A sleeve 15 of radiopaque material is inserted inside and firmly joined to the hollow cylindrical body 13 of the marker element 1.

For a woven stent made up of 24 wires, an embodiment of the marker element 1 with, for example, three projections/anchors 14 arranged at 120° angles is preferable. Depending on the number of weave wires or the nature of the stent 2, woven or laser cut, other numbers of projections/anchors 14 can be chosen or they can even have a staggered arrangement along the central axis 18 of the hollow cylindrical body 13.

The projections/anchors 14 pass through the mesh holes 20 or the weave of the folded stent 2. The projections/anchors 14 should preferably be realized as prisms or truncated pyramids without undercutting, so that the stent 2, when it expands radially during deployment, easily detaches itself from the marker element 1.

The hollow cylindrical body 13 with the projection(s)/anchor(s) should preferably be made from a plastic suitable for medical use, for example polyoxymethylene (POM) using the injection moulding procedure. The sleeve 15 should preferably be made of a very radiopaque metal or an alloy, for example gold, platinum, tantalum, or a platinum-iridium alloy.

Figure 3:
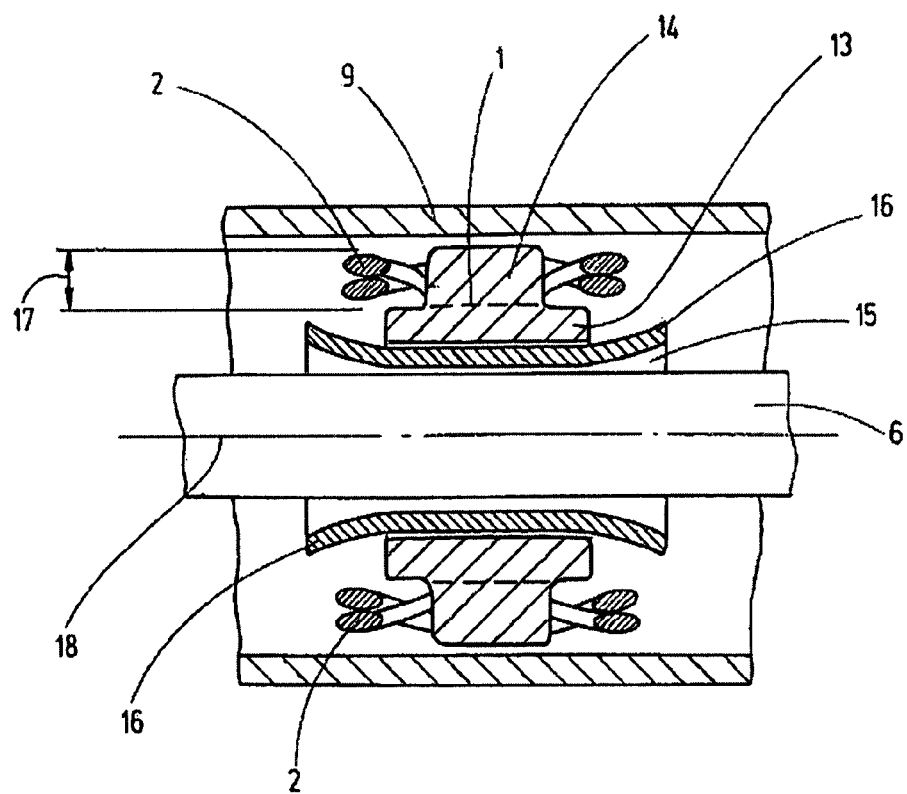
FIG. 3 shows an enlarged, schematic, view, which is not true to scale, of a longitudinal section of the marker element from FIG. 2.

FIG. 3 shows an enlarged, schematic and not true to scale longitudinal section of the marker element from FIG. 2. In the embodiment of the marker element 1 shown, the sleeve 15 is positively secured to the hollow cylindrical body 13 by widenings 16 on both sides 15. This ensures that the sleeve 15 cannot become detached from the hollow cylindrical body 13 in the direction of the central axis 18.

A press fit between sleeve 15 and hollow cylindrical body 13 would be conceivable in another embodiment, but this could lead to overstressing and breakage of the hollow cylindrical body 13 by stress-inducing mechanical creep processes. The sleeve 15 could then become detached in the direction of the central axis 18. There must be sufficient play between the sleeve 15 and the guide wire catheter 6 so that it, or rather the marker element 1, can easily slide along the guide wire catheter 6.

The height 17 of the projections/anchor 14 is designed to be sufficient to ensure that the folded stent 2 cannot slip between the outer sleeve 9 and the projection/anchor 14 from the marker element 1 in the direction of the central axis 18. However, the height 17 of the projection/anchor 14 must be low enough to ensure that the marker element 1 cannot get jammed in the outer sleeve 9.

A widening 16 of the sleeve 15 ensures that, when the marker element 1, still coupled to the stent 2, slides on the guide wire catheter 6 when stent 2 is deployed, the marker element 1 does not become jammed or wedged on the guide wire catheter 6.

Figure 4:
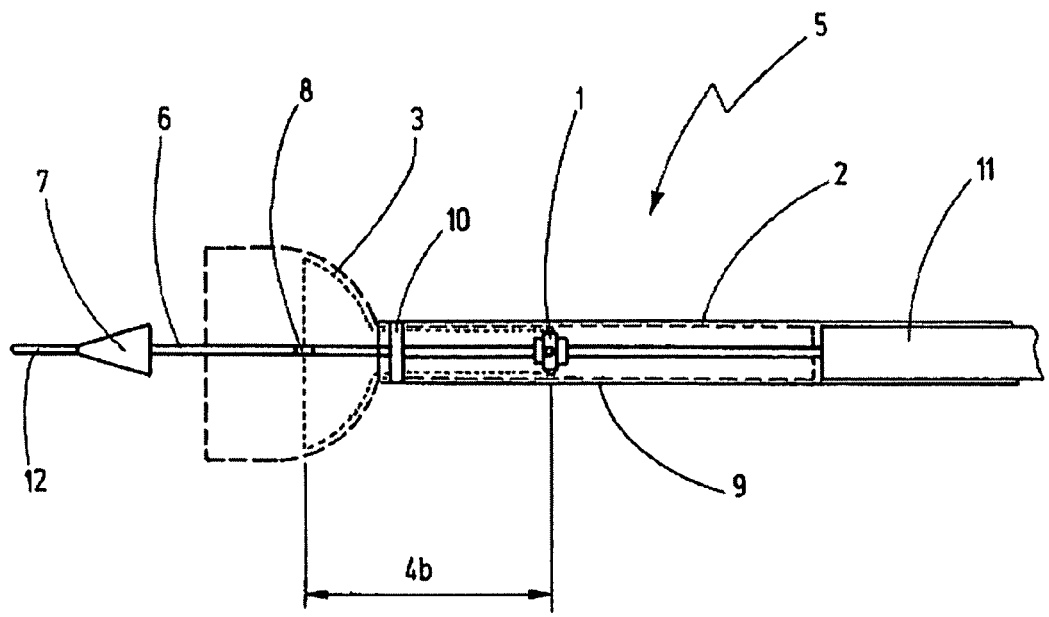
FIG. 4 shows a schematic representation of the distal part of the delivery system from FIG. 1 with the partly deployed stent, in which the distal half of the functional zone of the stent has already been released.
Figure 5:
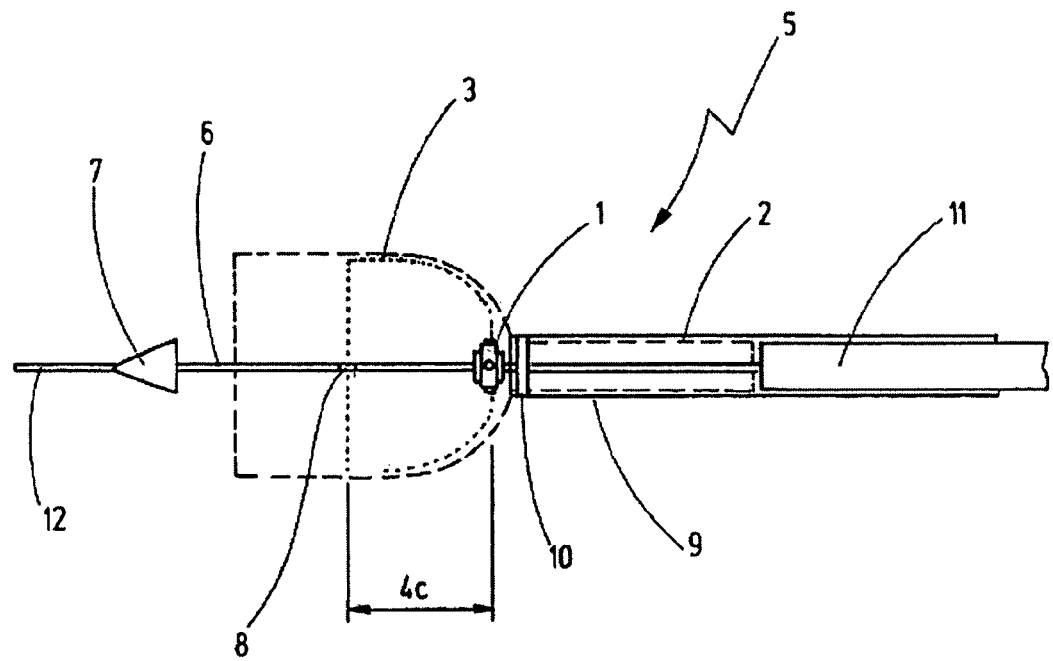
FIG. 5 shows a schematic representation of the distal part of the delivery system from FIG. 1 with the partly deployed stent, showing how the proximal end of the functional zone emerges.
Figure 6:
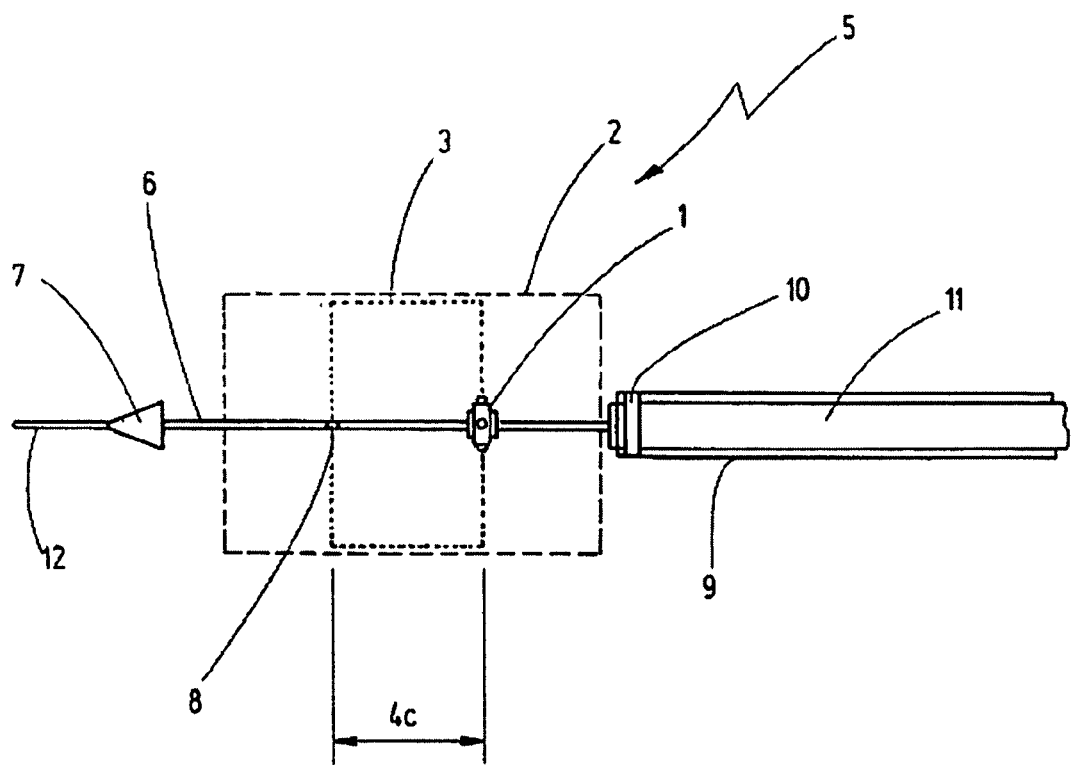
FIG. 6 shows a schematic diagram of the distal part of the delivery system from FIG. 1 with the fully deployed stent.

FIGS. 4 to 6 show the process of the deployment of a stent 2 from the distal part of the delivery system 5 from FIG. 1. In FIG. 4, part of the stent 2 has been deployed. The distal half of its functional zone 3 has passed the outer sleeve marker 10, as can be seen under fluoroscopy. The marker element 1 has now moved distally relative to the guide wire catheter 6. The length 4b of the functional zone 3 of the partly deployed stent 2 is thus shorter than the length 4a in the starting condition, shown in FIG. 1. Because of their structure, the stent 2, and thus also its functional zone 3, have already contracted.

In FIG. 5, an even greater part of stent 2 is shown as deployed or released. The proximal end of its functional zone 3 has just passed the outer sleeve marker 10. Stent 2 has further shortened. The length 4c of the functional zone 3 has thus further shortened with respect to length 4b in FIG. 4. As already mentioned, for woven stents this shortening reduces the length to as little as a sixth of the length in the folded state. As a result of its positive fit to the stent 2 due to its anchors 14, the marker element 1 has moved further in a distal direction relative to the guide wire catheter (6).

FIG. 6 shows the distal part of the delivery system 5 from FIG. 1 together with the fully deployed stent 2. In this state, stent 2 has become detached from the marker element 1 radially outwards. The structure of stent 2 has further shortened. The length 4c of the functional zone 3 of stent 2 and the position of the marker element 1 which has now detached from stent 2 remain constant.

After deployment of stent 2, the delivery system 5 and the mobile marker element 1 attached to it are withdrawn from the body vessel.

LIST OF REFERENCE NUMBERS

1 Marker
2 Stent
3 Functional zone (of stent (2))
4a Length (of functional zone (3) of stent (2) in the delivery system (5))
4b Length (of functional zone (3) of the partly deployed stent (2))
4c Length (of the completely released functional zone (3))
5 Delivery system
6 Guide wire catheter/tubular element
7 Tip
8 Guide wire catheter marker
9 Outer sleeve
10 Outer sleeve marker
11 Pusher
12 Guide wire
13 Hollow cylindrical body
14 Anchor
15 Sleeve
16 Widening
17 Height (of anchor 14)
18 Central axis
19 Grip
20 Mesh

The invention claimed is:

1. Device for the delivery of a self-expanding stent into a body vessel, the device having
   a self-expanding stent having a mesh,
   a tubular element which is guided through the stent
   a marker element for marking one or more boundaries within a section of said self-expanding stent, the marker element including a radiopaque material
   wherein the marker element, being located between said stent and said tubular element, is slidably mounted on said tubular element and engages detachably into the mesh of said stent, wherein said marker element consists of a hollow cylindrical element and a sleeve body, wherein the hollow cylindrical element has at least one radially outward-pointing projection which engages into the mesh of the stent, and wherein the sleeve body fits inside the hollow cylindrical element of the marker element and is firmly connected to it.

2. Device according to claim 1, wherein the tubular element is a guide wire catheter.

3. Device according to claim 1, wherein said marker element detaches from the stent during deployment and expansion of the stent.

4. Device according to claim 1, wherein said marker element marks an end of a functional zone of the stent, the functional zone representing a section of the stent with a lower weaving angle than the adjoining sections of the stent in a longitudinal direction.

5. Device according to claim 1, wherein said hollow cylindrical element has 1 to 12 radially outward-pointing projections which engage into the mesh of the stent.

6. Device according to claim 1, wherein said at least one projection has the form of a prism or of an pyramid.

7. Device according to claim 1, wherein said marker element is made completely of radiopaque material.

8. Device according to claim 1, wherein said sleeve body contains a radiopaque material and the hollow cylindrical element consists of at least one non-radiopaque material.

9. Device according to claim 1, wherein said sleeve body has widenings at its moving ends to prevent the hollow cylindrical element into which the sleeve is inserted becoming detached from the sleeve.

10. Marker element for marking one or more boundaries within a section of a self-expanding stent having a mesh, the marker element including a radiopaque material and being fitted on a device for the delivery of the stent into a body vessel, wherein the device comprising a tubular element which is guided through the stent, wherein the marker element detachably engages with the meshes of the stent when the stent is radially compressed, wherein the marker element between the stent and the tubular element is slidably mounted on the tubular element, and wherein said marker element consists of a hollow cylindrical element and a sleeve body, wherein the hollow cylindrical element has at least one radially outward-pointing projection which engages into the mesh of the stent, and wherein the sleeve body fits inside the hollow cylindrical element of the marker element and is firmly connected to it.

* * * * *